(12) United States Patent
Langley et al.

(10) Patent No.: US 7,198,615 B2
(45) Date of Patent: Apr. 3, 2007

(54) INJECTION DEVICE

(75) Inventors: Christopher Nigel Langley, Leamington Spa (GB); Robert Woolston, Moreton Morrell (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 10/471,718

(22) PCT Filed: Mar. 26, 2002

(86) PCT No.: PCT/GB02/01437

§ 371 (c)(1), (2), (4) Date: Sep. 15, 2003

(87) PCT Pub. No.: WO02/076537

PCT Pub. Date: Oct. 3, 2002

(65) Prior Publication Data

US 2004/0122368 A1    Jun. 24, 2004

(30) Foreign Application Priority Data

Mar. 27, 2001    (GB)    ................................. 0107600.9

(51) Int. Cl.
  *A61M 1/00*     (2006.01)
  *A61M 37/00*    (2006.01)
(52) U.S. Cl. ........................ 604/151; 604/154; 604/155
(58) Field of Classification Search ................ 604/151, 604/155, 181, 187, 207–211, 218, 224
See application file for complete search history.

(56) References Cited

U.S. PATENT DOCUMENTS 4,313,439 A * 2/1982 Babb et al. .................... 604/28
4,860,507 A * 8/1989 Garza-Tamez ............. 52/167.4
6,045,537 A * 4/2000 Klitmose ..................... 604/224
6,482,186 B1 * 11/2002 Douglas et al. ............. 604/218
6,796,970 B1    9/2004 Klitmose et al.

FOREIGN PATENT DOCUMENTS

EP        0 235 905 A1    9/1987

* cited by examiner

*Primary Examiner*—Catherine S. Williams
(74) *Attorney, Agent, or Firm*—Oliff & Berridge, PLC

(57) ABSTRACT

Injection devices are known for the self administration of medicament by patients in which medicament is typically contained within a cartridge located within the injection device. It is a problem that injection devices should be small enough to fit into a jacket pocket or a hand bag without difficulty. Also, the injection device must be of a size that enables a piston or similar used to drive a cartridge bung within the cartridge to be moved both to a maximum dispense position within the cartridge and to be fully withdrawn from the cartridge to allow for replacement of the cartridge. A drive mechanism for an injection device is disclosed in which a second piston (42) is successively moved in relation to a first end of a medicament cartridge (8) containing a medicament selectively to drive a bung (10) into the medicament cartridge (8), the drive mechanism comprising a means (36) defining a passageway (38), a first piston (40) and the second piston (42), in which the passageway (38) has a first end and a second end, the first piston (40) closing the first end of the passageway (38) and a first end of the second piston (42) closing the second end of the passageway (38) to define a chamber in the passageway (38), a non-compressible medium being contained within the chamber such that a first relative movement in a first direction at the first end of the passageway (38) results in a second relative movement in a direction opposite the first direction at the second end of the passageway (38).

6 Claims, 4 Drawing Sheets

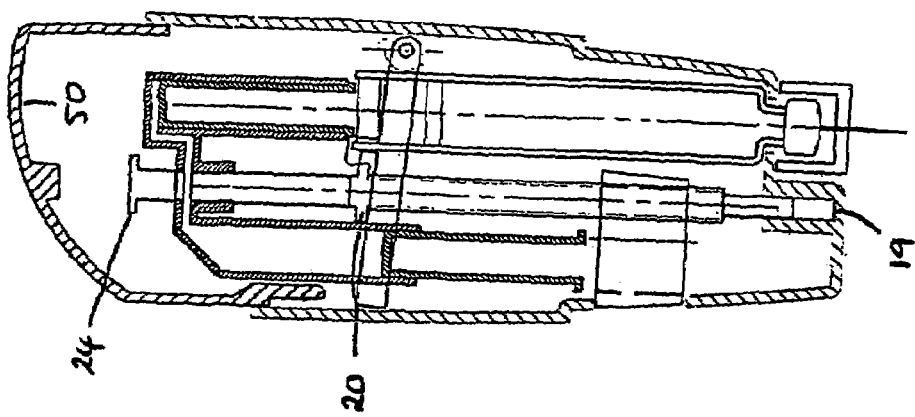
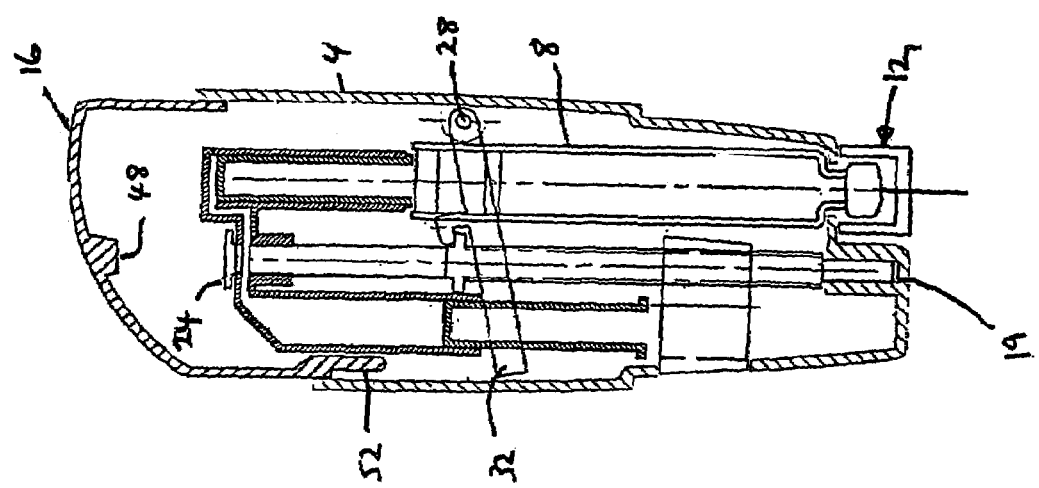
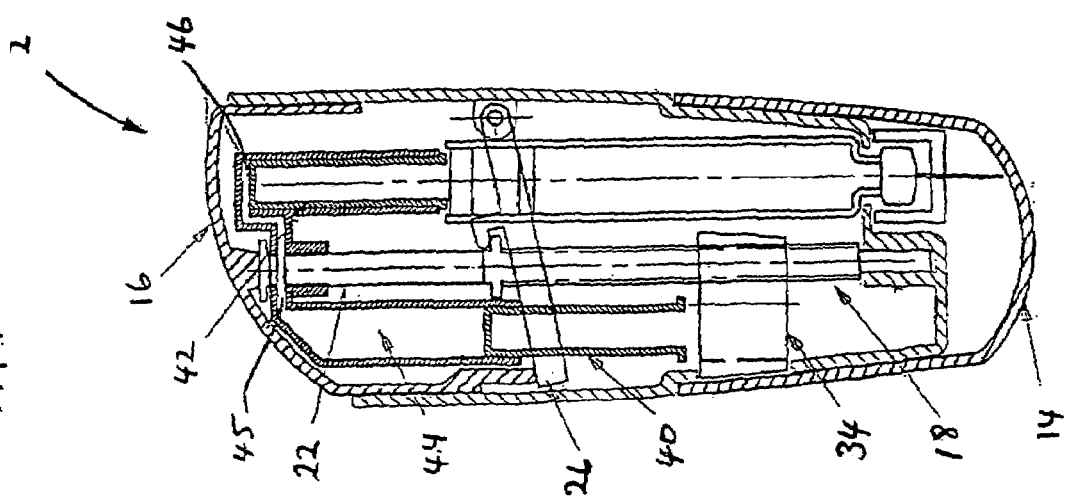

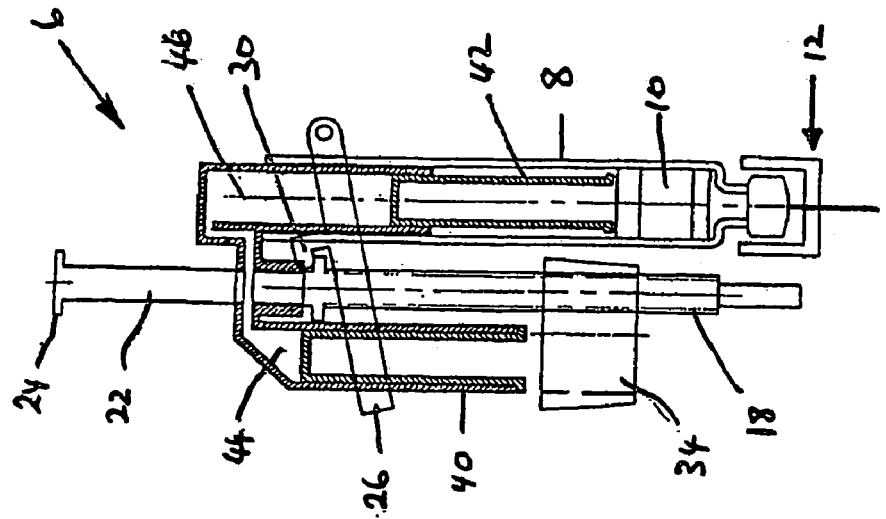
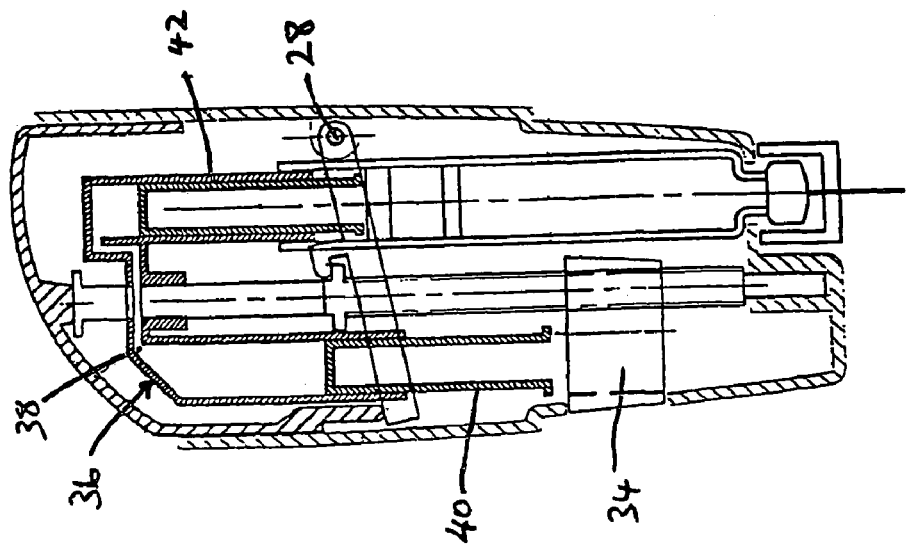

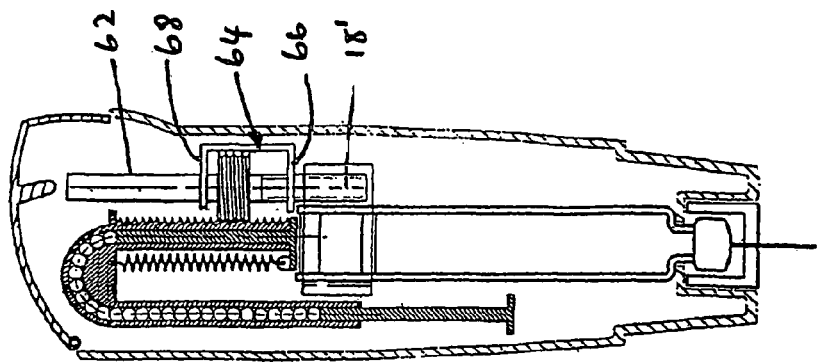
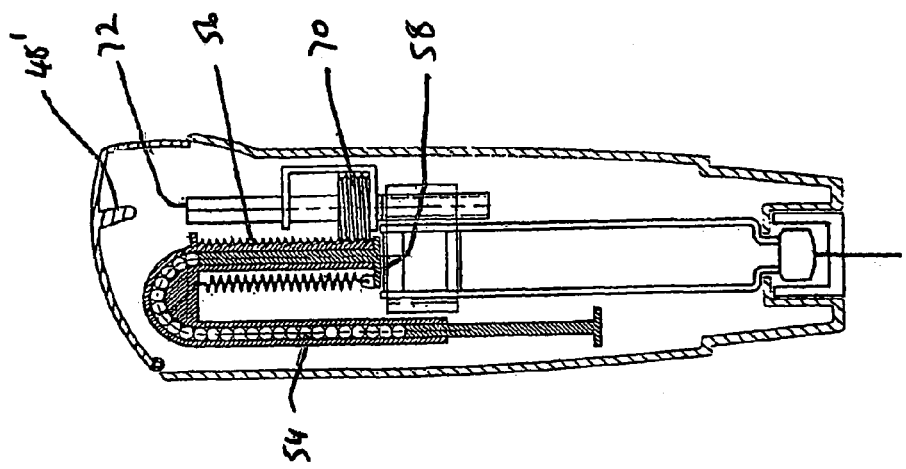
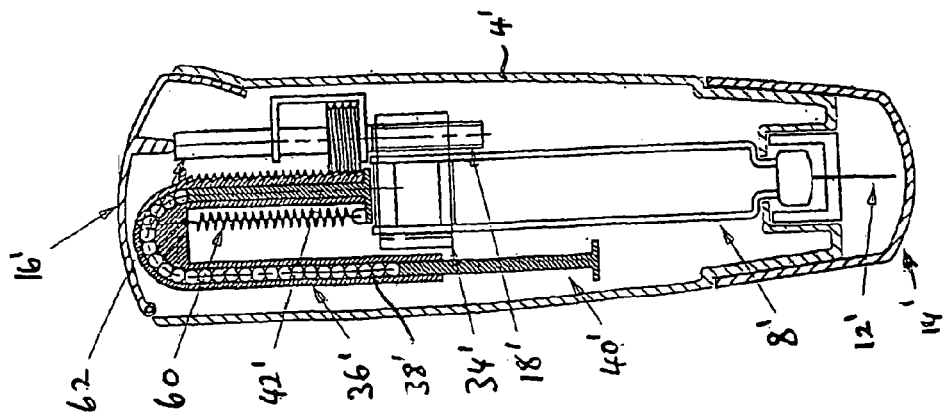

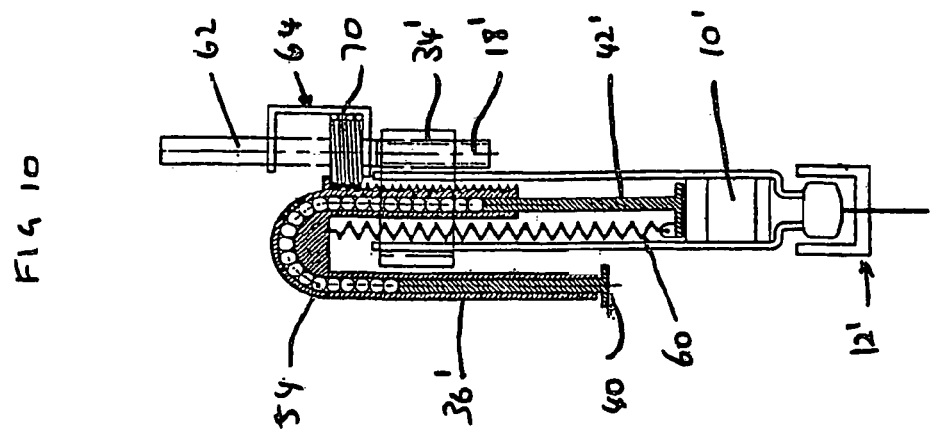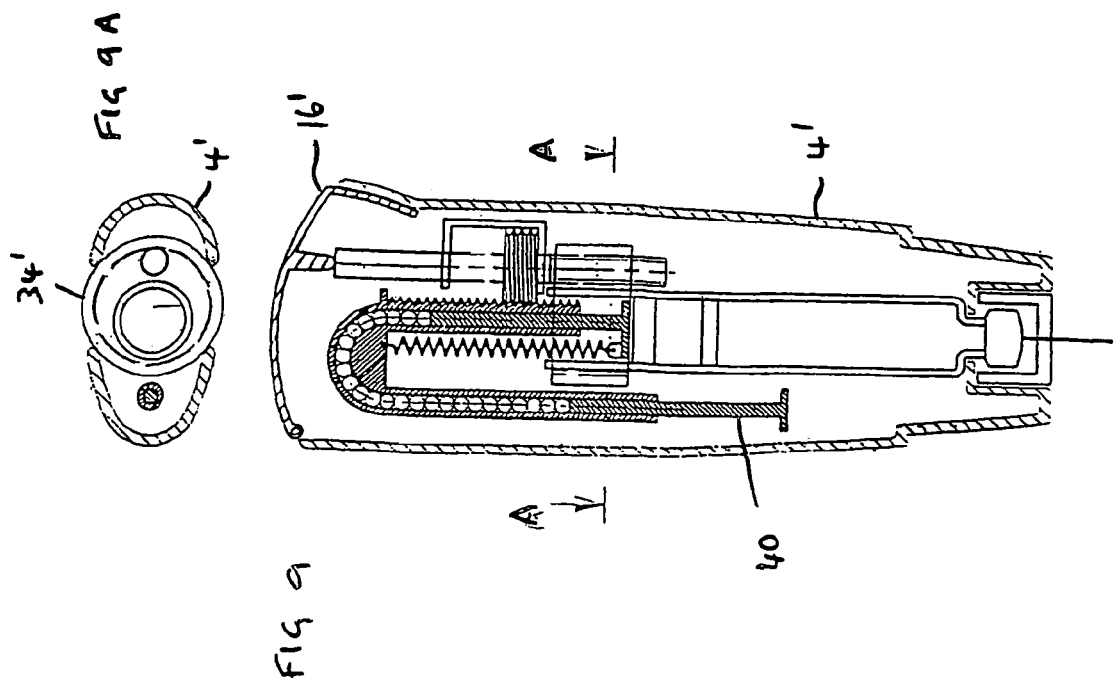

INJECTION DEVICE

The present invention relates to improvements in an injection device, and in particular to improvements in a portable injection device for dispensing controlled quantities of a medicament.

Injection devices are known for the self administration of medicament by patients. For example, those suffering from diabetes may require regular injections of insulin. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the infirm, those suffering from vision difficulties and others suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

It is an advantage of the present invention that it provides a solution to these conflicting requirements.

According to a first aspect of the present invention, a drive mechanism for an injection device in which a second piston is successively moved in relation to a first end of a medicament cartridge containing a medicament selectively to drive a bung closing a first end of the medicament cartridge into the medicament cartridge to expel medicament through a delivery member located at a second end of the medicament cartridge, is characterised in that the drive mechanism comprises a means defining a passageway, a first piston and the second piston, in which the passageway has a first end and a second end, the first piston closing the first end of the passageway and a first end of the second piston closing the second end of the passageway to define a chamber in the passageway, a non-compressible medium being contained within the chamber such that a first relative movement in a first direction at the first end of the passageway results in a second relative movement in a direction opposite the first direction at the second end of the passageway.

Preferably, the drive means further comprises a dose setting device to control the relative movement.

According to a second aspect of the present invention, an injection device comprising a housing and a driver mechanism according to the first aspect of the present invention is characterised in that the first piston is fixed with respect to the housing.

Preferably, the non-compressible medium comprises anon-compressible fluid Alternatively, the non-compressible medium comprises a plurality of non-compressible elements. Preferably, the non-compressible elements comprise a plurality of bearings.

Preferably, the dose setting device comprises a spline, means to rotate the spline, a threaded member, and a control lever, the threaded member being connected to the spline and through the means defining the passageway, the control lever being pivotally connected to the housing, the spline and the control lever being provided with interengaging means, such that rotation of the spline causes movement of the control lever and movement of the threaded member through the means defining the passageway.

Alternatively, the dose setting device comprises a spline, means to move the spline, a threaded member mounted upon a moveable shaft for engagement of the threaded member with the means defiling the passageway, such that movement of the spline causes movement of the threaded member with respect to the means defining the passageway.

The invention will now be described, byway of example only, with reference to the accompanying drawings in which:

FIG. 1 shows in side section a first embodiment of an injection device according to the present invention;

FIG. 2 shows a similar view with the cover removed and the injection device ready, FIG. 3 shows a view similar to FIG. 2 after dialling of a required dosage;

FIG. 4 shows a view similar to FIG. 3 after delivery of the required dosage;

FIG. 5 shows a side section of a mechanism for use with the injection device of FIGS. 1 to 4;

FIG. 6 shows in side section a second embodiment of an injection device according to the present invention;

FIG. 7 shows a similar view to FIG. 6 with the cover removed and the injection device ready;

FIG. 8 shows a view similar to FIG. 7 after dialling of a required dosage, FIG. 9 shows a view similar to FIG. 8 after delivery of the required dosage;

FIG. 9A shows a section along line A—A in FIG. 9; and

FIG. 10 shows a side section of a mechanism for use with the injection device of FIGS. 6 to 9.

Like reference numerals will be used to refer to like parts of the injection device.

Referring first to FIGS. 1 to 5, there may be seen a first embodiment of an injection device having a drive mechanism in accordance with the present invention.

The injection device 2 has a main housing 4 within which a drive mechanism 6 is located A medicament cartridge 8 is shown in position within the main housing 4. The medicament cartridge 8 has a flexible membrane at one end and a displaceable bung 10 at the other. A delivery member in the form of a needle unit 12 is secured to a first end of the main housing 4 such that a needle pierces the flexible membrane of the medicament cartridge 8. A cover 14 is provided over the first end of the main housing 4 to protect the needle unit from damage and a user from inadvertent pricking by the needle. A button 16 is provided at a second end of the main housing 4. The button 16 is in the form of a cup or cap which is adapted for sliding movement with respect to the main housing 4. The button 16 has a stop 48 formed on an inner surface 50 there of which may abut with the radially extending flange 24 of the threaded member 22.

A spline 18 is located generally centrally within the main housing 4. As may be seen one end of the spline 18 is located within a bore 19 provided in the first end of the main housing 4. The spline 18 is provided about a fast portion with a radially extending collar 20. A threaded member 22 extends from the spline 18. The threaded member 22 is provided with a radially extending flange 24 at an end remote from the spline 18.

A control lever 26 is provided within the main housing 4. A first end of the control lever 26 is secured at a pivot point 28 to the main housing 4. The control lever 26 is provided at an intermediate position with a finger or fingers 30 which engage with the radially extending collar 20 of the spline 18. A free end of the lever 32 is located in the path of a leading edge 52 of the button 16.

A dial/dose mechanism 34 is located in the main housing 4 and is connected to the threaded member 22 by the spline18.

The drive mechanism 6 comprises a means 36 defining a passageway 38, the passageway 38 having a first end and a second end, each of the first and second ends of the passageway being closed by respective first and second pistons. The means 36 defining the passageway may conveniently take the form of a secondary housing. The first piston 40 is fixed relative to the man housing 4. The threaded member 22 passes through the means defining the passageway. A first end of the second piston 42 closes the passageway 38, a second end is located adjacent the medicament cartridge bung 10. As can be seen from FIGS. 1 and 2 the passageway 38, when the medicament cartridge 8 is full and no dosage has been dialled, comprises a first chamber 44 of relatively large volume adjacent the first piston 40 and a second chamber 46 of relatively small volume adjacent the second piston 42; the first and second chambers 44,46 being connected by an interconnecting portion 45 of the passageway 38.

To operate the injection devices 2, the button 16 is released to adopt the position shown in FIG. 2.

A dosage is then dialled using the dose/dial mechanism 34. As maybe seen from FIG. 3, this has the effect of rotating the threaded member 22 through the means defining the passageway and drawing the spline 18 from the bore 19 by a specified amount, thereby causing the control lever26 to pivot.

The button 16 is then depressed by a user. On depression of the button 16 by the user, a leading edge 52 of the button 16 abuts then drives the free end 32 of the control lever 26 causing the control lever26 to pivot This draws the spline 18 towards the first end of the main housing 4. This in turn draws the threaded member 22 and thus the means defining the passageway to be drawn towards the first end of the main housing 4.

In particular, since the first piston 40 is fixed with respect to the main housing 4, the movement of the means defining the passageway causes the first chamber 44 to become smaller in volume and the second chamber 46 in turn to become correspondingly larger thereby driving the second piston 42 out of the means defining the passageway. This in turn causes the bung 10 in the medicament cartridge 8 to be displaced towards the needle unit thereby expelling medicament from the medicament cartridge (FIG. 4). The change in relative size of the first and second chambers, and thereby movement of the bung 10, ceases when the stop 48 on the button 16 abuts the radially extending flange 24 of the threaded member 22.

Further dosages of medicament maybe dialled and dispensed as required or until the bung 10 has been displaced as far as is possible within the medicament cartridge 8 (FIG. 5). At this stage, the threaded member 22 has been precessed as far as possible through the means defining the passageway.

After repeated dosages have been dispensed; the drive mechanism 6 is reset causing the means defining the passageway to be returned to the initial position shown in FIG. 2 such that the second piston 42 is withdrawn into the means defining the passageway and out of the medicament cartridge 8. The medicament cartridge 8 may then be replaced.

Referring now to FIGS. 6 to 10, there may be seen a second embodiment of an injection device having a drive mechanism in accordance with the present invention.

The injection device 2' has a main housing 4' within which a drive mechanism 6' is located. A medicament cartridge 8' is shown in position within the main housing 4'. The medicament cartridge 8' has a flexible membrane at one end and a displaceable bung 10' at the other. A delivery member in the form of a needle unit 12' is secured to a first end of the main housing 4' such that a needle pierces the flexible membrane of the medicament cartridge 8'. A cover 14' is provided over the first end of the housing to protect the needle unit from damage and a user from inadvertent pricking by the needle. A button 16' is provided at a second end of the main housing 4'. The button 16' is adapted for pivoting movement with respect to a second end of the main housing 4'. A stop 48' is provided on an underside of the button 16'.

Means 36' to define a passageway 38' are provided in the main housing 4'. A first piston 40' is provided fixed in relation to the main housing 4'. A first end of the first piston 40' extends into and closes one end of the passageway 38'. A second piston 42' closes a second end of the passageway 38'. The passage way 38' contains a plurality of non-compressible elements. In the embodiment illustrated a plurality of ball bearings 54 are shown. The means defining the passage way is provided with a toothed or threaded region 56 in the vicinity of the second piston 42'. An end of the second piston 42' exterior to the passageway is provided with a flange 58. This end of the second piston 42' is in use located adjacent the bung 10' of the medicament cartridge 8'. Biasing means are provided between the flange 58 and the means defining the passageway. In the illustrated embodiment, the biasing means takes the form of a return spring 60.

A dial/dosage means 34' is also provided in the main housing 4. A spline 18' is connected to the dial/dosage means 34'. A dose setting spindle 62 is connected to the spline 18' for rotation about an axis. The spindle 62 is carried from a bracket 64 mounted in the main housing 4'. The bracket has first and second alms 66,68. The spindle 62 maybe displaced along its axis between the first and second aims 66,68 of the bracket 64. The spindle 62 is provided with a threaded portion 70. The threaded portion 70 of the spindle 62 is located intermediate the first and second aims 66,68 of the bracket 64. The threaded portion 70 of the spindle 62 engages with the toothed or threaded region 56 of the means defining the passageway.

To operate the injection device 2', the button 16' is released to adopt the position shown in FIG. 7. A dosage is then dialled using the dose/dial mechanism 34'. As may be seen from FIG. 8, this has the effect of rotating the threaded portion 70 of the spindle 62. This drives the spindle 62 and attached spline 18' from a rest position in which threaded portion 70 of the spindle 62 is located against the first arm 66 of the bracket 64 to a second position towards the second arm 68 of the bracket 64.

The user then depresses the button 16'. The stop 48' on the underside of the button 16'abuts a free end 72 of the spindle 62 driving the spindle 62 towards the first arm 66 of the bracket 64.

Since the spindle 62 does not rotate under the action of the stop 48', the means defining the passageway is driven towards the first end of the main housing 4'.

Since the first piston 40' is fixed with respect to the main housing 4', the non-compressible elements 54 move within the means defining the passageway to drive the second piston 42' out of the means defining the passageway. This in turn causes the bung 10' in the medicament cartridge 8' to be moved towards the needle unit thereby expelling medicament from the medicament cartridge (FIG. 9). Movement of the bung 10' ceases when the threaded portion 70 of the spindle 62 is returned to the rest position.

Further dosages of medicament may be dialled and dispensed as required or until the bung 10' has been displaced as far as is possible within the medicament cartridge 8' (FIG. 10). At this stage, the threaded portion 70 of the spindle 62 has reached the end of the toothed or threaded region 56 of the means defining the passageway.

After repeated dosages have been expelled, the mechanism is reset under the action of the biasing means causing the means defining the passage way to be returned to the initial position shown in FIGS. 6 and 7 such that the second piston 42' is withdrawn into the means defining the passageway and out of the medicament cartridge 8'. The medicament cartridge 8' may then be replaced The relative arrangement of the drive mechanism and the medicament cartridge 6 means that the main housing 4 provides a relatively large flat face where a relatively large dose display, such as a liquid crystal display may be located. This in turn enables the dose display to use relatively large figures or other characters. This is an advantage for those with impaired vision.

The invention claimed is:

1. A drive mechanism for use in an injection device having a main housing, whereby in said drive mechanism a second piston is successively moved in relation to a first end of a medicament cartridge containing a medicament selectively to drive a bung closing a first end of the medicament cartridge into the medicament cartridge to expel medicament through a delivery member located at a second end of the medicament cartridge, wherein said drive mechanism comprises a means defining a passageway, a first piston which is fixed to said housing and the second piston, in which the passageway has a first end and a second end, the first piston closing the first end of the passageway and a first end of the second piston closing the second end of the passageway to define a chamber in the passageway, a non-compressible medium comprising a fluid being contained within the chamber such that a first relative movement in a first direction at the first end of the passageway results in a second relative movement in a direction opposite the first direction at the second end of the passageway.

2. A drive mechanism according to claim 1, wherein the drive mechanism further comprises a dose setting device to control the relative movement.

3. An injection device comprising a main housing and the drive mechanism according to claim 1.

4. An injection device comprising a main housing and the drive mechanism according to claim 2.

5. An injection device according to claim 4, wherein the dose setting device comprises a spline, means to rotate the spline, a threaded member, and a control lever, the threaded member being connected to the spline and through the means defining the passageway, the control lever being pivotally connected to the housing, the spline and the control lever being provided with interengaging means, such that rotation of the spline causes movement of the control lever and movement of the threaded member through the means defining the passageway.

6. An injection device according to claim 4, wherein the dose setting device comprises a spline, means to move the spline, a threaded member mounted upon a moveable shaft for engagement of the threaded member with the means defining the passageway, such that movement of the spline causes movement of the threaded member with respect to the means defining the passageway.

* * * * *